United States Patent [19]

Black

[11] Patent Number: 4,868,491
[45] Date of Patent: Sep. 19, 1989

[54] APPARATUS FOR MONITORING THE MOISTURE CONTENT OF HAY AS IT IS BEING FORMED INTO A BALE

[76] Inventor: Grover R. Black, Rte. #3, Box 240, Cheney, Wash. 99004

[21] Appl. No.: 131,949

[22] Filed: Dec. 11, 1987

[51] Int. Cl.⁴ ............................................. G01R 27/02
[52] U.S. Cl. ..................................... 324/65 R; 73/73; 324/65 P; 340/104
[58] Field of Search ............... 324/65 R, 65 P; 73/73; 340/604

[56] References Cited

U.S. PATENT DOCUMENTS

| | | |
|---|---|---|
| 2,003,077 | 5/1935 | Heppenstall . |
| 2,342,553 | 2/1944 | Olpin . |
| 2,621,232 | 12/1952 | Spalding . |
| 2,653,298 | 9/1953 | McKinley .................. 324/65 R |
| 2,742,541 | 4/1956 | Bunting . |
| 2,757,602 | 8/1950 | Nolt . |
| 2,852,740 | 9/1958 | Posey et al. ................ 324/65 R |
| 3,005,154 | 10/1961 | Moore et al. . |
| 3,412,326 | 11/1968 | Jones et al. ................ 324/65 R |
| 3,482,162 | 12/1969 | Wochnowski . |
| 3,563,013 | 2/1971 | Elfes . |
| 3,875,504 | 4/1975 | Bodycomb, Jr. et al. . |
| 3,950,698 | 4/1976 | Wochnowski . |
| 3,994,156 | 11/1976 | Koster . |
| 4,451,781 | 5/1984 | Anderson . |
| 4,453,460 | 6/1984 | Rabe et al. . |
| 4,604,857 | 8/1956 | Maher . |
| 4,812,741 | 3/1989 | Stowell .............................. 324/65 P |

FOREIGN PATENT DOCUMENTS 60-186744 9/1985 Japan .

OTHER PUBLICATIONS

"New Products", *Hay & Forage Growers*, Aug. 1987, p. 12.

*Primary Examiner*—Reinhard J. Eisenzopf
*Assistant Examiner*—Robert W. Mueller
*Attorney, Agent, or Firm*—Wells, St. John & Roberts

[57] ABSTRACT

An improved hay baler and a moisture sensor for monitoring the moisture content of hay as it is being formed into a bale is disclosed. The sensor is adapted for mounting internally to the side of a baling chamber. It includes a pair of spaced apart elongated electrodes supported on an insulating material and exposed for contacting hay passing through the baling chamber. The electrodes are connected to a resistance network for measuring the electrical resistance in hay passing between the electrodes. An indicator is in electrical communication with the resistance network for indicating the moisture content in the hay being formed into a bale to an operator.

4 Claims, 3 Drawing Sheets

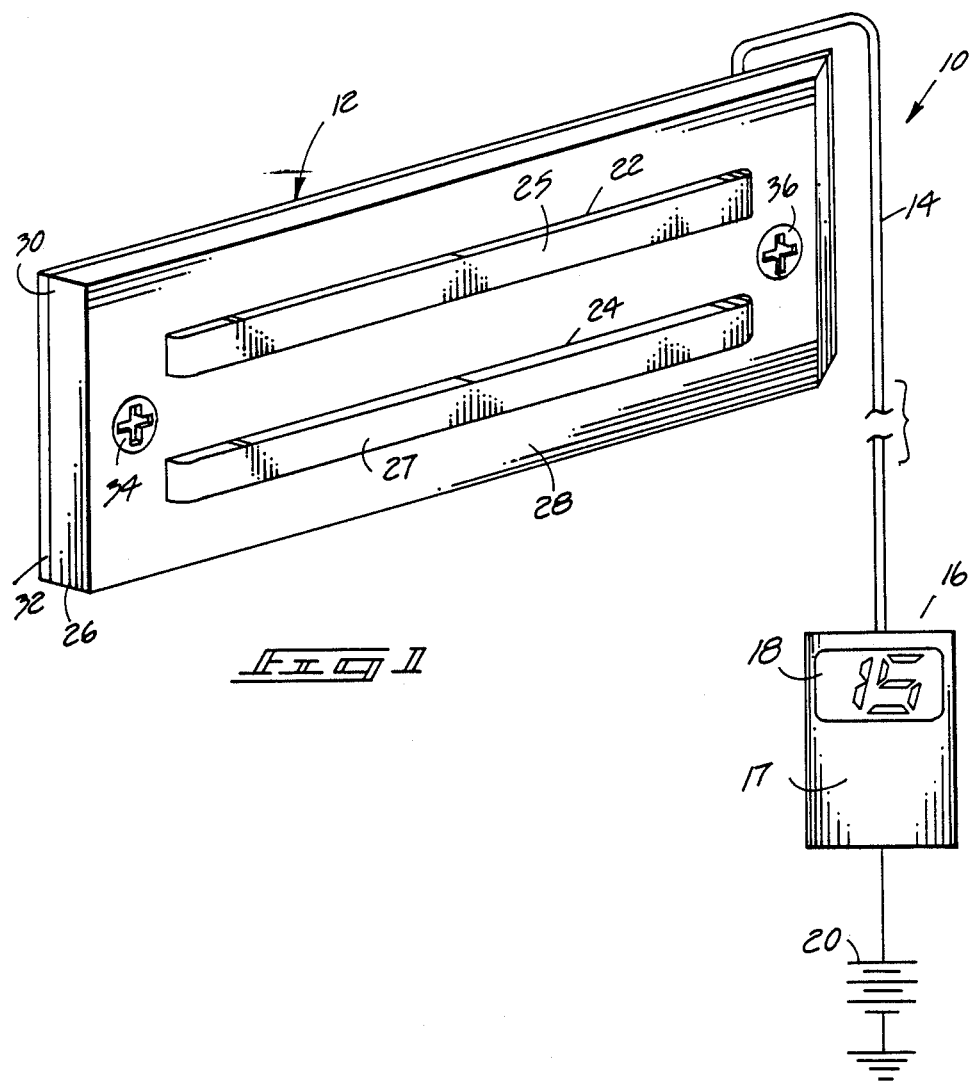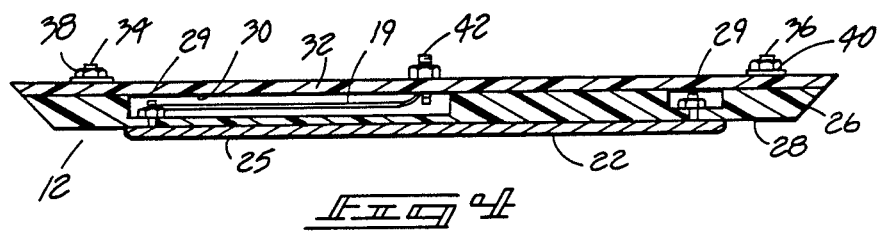

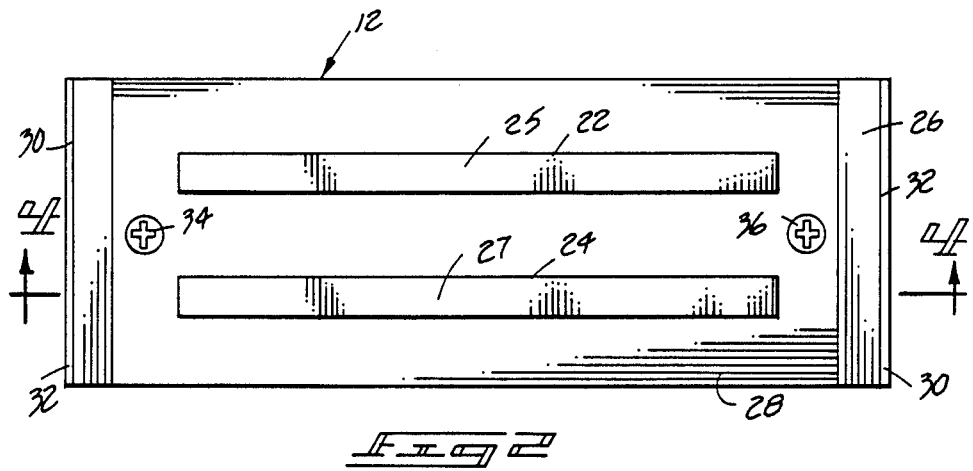
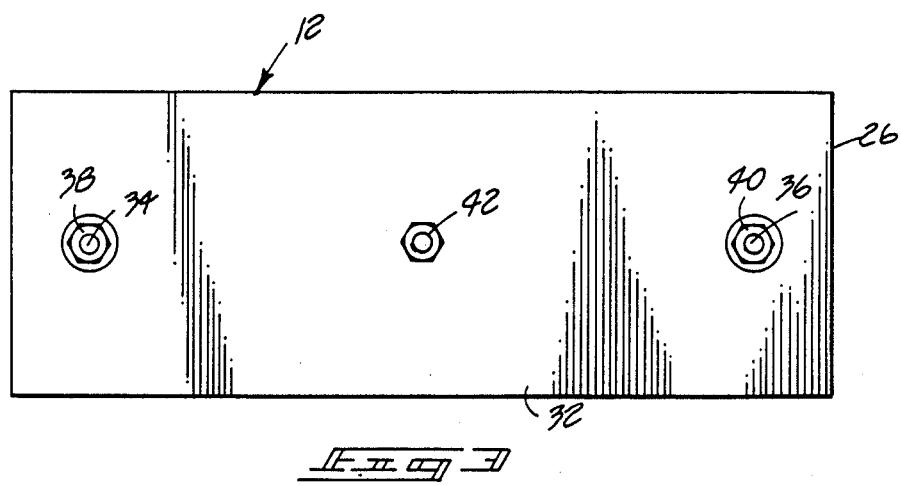

APPARATUS FOR MONITORING THE MOISTURE CONTENT OF HAY AS IT IS BEING FORMED INTO A BALE

TECHNICAL FIELD

This invention relates generally to hay baling, and more particularly to the determination of the moisture content of hay.

BACKGROUND OF THE INVENTION

The moisture content of a bale of hay should be within a predetermined range to be acceptable as feed for livestock and for safe storage.

The present accepted method for determining moisture content of hay is to repeatedly probe a finished bale with a long pointed object having a moisture sensor at its end to provide a reading of moisture content. The probe must be inserted into the bale in different locations to get an estimate of the average moisture content of the hay in the bale. The mositure readings from different insertion points of the probe can vary substantially. This requires the farmer to estimate an average moisture content using a wide range of readings, experience, and some intuition. Additionally, to be sure the hay farmer is producing hay bales of a desired moisture content, the operator must periodically stop to obtain a series of moisture readings of recently produced bales with the sensing probe. Such testing wastes an insidious amount of time and can result in the production of a number of bales having unacceptable moisture content in the time elapsed since the last tests of the bales.

U.S. Pat. No. 4,451,781 to Anderson describes a moisture tester for cut hay which utilizes concentric electrodes mounted on the sidewall of a hay baler. The electrodes are stated to be positioned so that they contact the newly severed ends of the baled hay. The electrodes are connected to digital circuitry for providing a readout of moisture content. Another commercially available baler moisture sensor presently on the market utilizes spaced circular button electrodes for a similar purpose.

Actual experimentation with small circular spaced electrodes has shown that the resulting moisture readings are too susceptible to momentary changes in measured resistance. There is also substantial opportunity for lack of engagement between the cut ends of the hay pressing into the baler and the relatively small sensors. More importantly, they simply cannot contact sufficient area along the bale as it is being formed to assure consistent and continuous moisture monitoring.

Accordingly, a need remains for an improved hay baler having a moisture sensing apparatus which instantaneously indicates to the hay farmer the moisture content of hay while it is being compacted into a bale.

DESCRIPTION OF THE DRAWINGS

The preferred embodiment of the invention is illustrated in the accompanying drawings, in which:

FIG. 1 is a diagrammatic view of the components of a moisture sensor apparatus in accordance with the invention;

FIG. 2 is a front elevational view of the sensing portion of the apparatus of FIG. 1;

FIG. 3 is a rear elevational view of FIG. 2;

FIG. 4 is a top view of FIG. 2;

DETAILED DESCRIPTION OF THE PREFERRED EMBODIMENT

Figure 5:
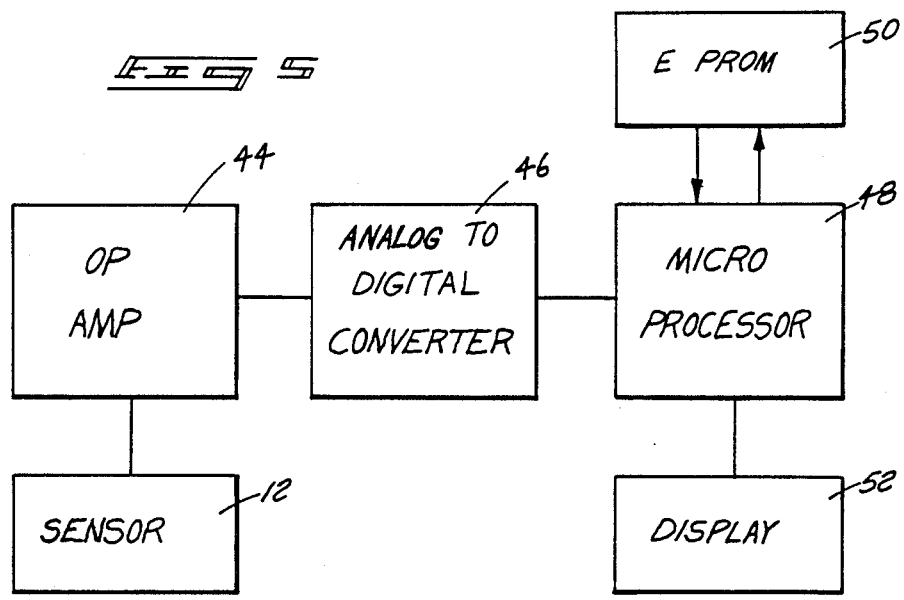
FIG. 5 is a schematic block diagram of the sensor and associated electronic components.

The following disclosure of the invention is submitted in compliance with the constitutional purpose of the Patent Laws "to promote the progress of science and useful arts" (Article 1, Section 8).

Referring to FIG. 1, a moisture sensing apparatus in accordance with the invention is indicated generally by reference numeral 10. The apparatus 10 is adapted for monitoring the moisture content of hay as it is being formed into a bale as successive compressed charges of hay moving longitudinally along a path within a baling chute of a hay baler. It comprises a sensor 12 which is adapted for mounting within the baling chute of a hay baler. Sensor 12 is electrically connected by means of cable 14 to a resistance monitoring means 16 mounted within a casing 17. Cable 14 is preferably long enough that casing 17 can be positioned in the tractor cab (not shown) which pulls the hay baler. Resistance monitoring means 16 measures the electrical resistance in hay passing adjacent to sensory component 12. The resistivity of hay varies with its moisture content, enabling moisture readings to be determined by measuring the electrical resistance of the hay contacting sensor 12.

The resistance monitoring means 16 includes processing means for converting resistance measurements to values indicative of the moisture content in the hay. The values of moisture content are indicated to an operator in the form of a changeable numeric display 18 positioned on the face of housing 17. The processing means is preferably adapted to convert electrical resistance values to numeric weight percents. Other indication means, such as an audible alarm, could also be used to indicate to the farmer when moisture content falls outside a predetermined range. Necessary power for operating the moisture sensor is provided from the grounded 12-volt battery system 20 of the hay baler or a tractor which pulls the baler. An alternate electrical power source could of course be used.

Referring to FIGS. 2-4, sensor 12 includes a pair of elongated electrodes 22, 24 spaced parallel to one another. Electrodes 22, 24 are mounted on a mass or block 26 of insulating material, such as polypropylene plastic. Insulating block 26 includes an exposed face 28 and a rear face 30. Electrodes 22, 24 include outer exposed surfaces 25, 27 respectively, and are mounted within insulating material 26 such that they engage the exposed face 28 of insulating block 26.

Electrodes 22, 24 extend to the rear face 30 of insulating block 26 for electrical connection to a standard RF coaxial cable jack 42. During manufacture, an insulative back plate 32 is bonded to rear face 30 of block 26 to shield the connections to the jack from all external contact or interference with any metal objects. Back plate 32 can be made of the same insulative material as block 26.

A pair of bolts 34, 36 extend rearwardly through holes formed in insulating block 26 and back plate 32. The holes in insulating block 26 are enlarged at exposed face 28 such that the heads of bolts 34, 36 are generally flush with face 28. Each of bolts 34, 36 include complementary nut and washer combinations 38, 40 respectively. Bolts 34, 36 are adapted to be received through mounting holes in a baling chute of a hay baler, with nuts 36, 38 being threaded to the bolts. Accordingly, the bolts and nuts provide a form of an attachment means for securing sensor 12 within the baling chute and exposing electrodes 22, 24 to hay passing through the chute.

A hole is also to be provided in the baling chute of the hay baler to freely receive coaxial jack 42. The hole in the baling chute should be large enough such that the jack and a connector of a cable 14 connected to it do not contact the metal baling chute.

The remaining components of apparatus 10 includes cable 14, which is in the form of coaxial conductors connected to jack 42. Cable 14 extends to casing 17, which houses the resistance network, processing means, and moisture indicator display. As stated previously, casing 17 is preferably positioned within the cab of the tractor which pulls the baler for ease of viewing by the farmer.

Referring to FIG. 5, the electronic components by which information is obtained and processed are illustrated in a block diagram. An operational amplifier 44 is provided to amplify the electrical signals obtained from sensory component 12. An analog to digital converter 46 converts the amplified electrical signals to digital form for manipulation by a central microprocessing unit 48. A suitably programmed E-PROM 50 controls operation of microprocessor 48 and directs a numeric display 52 for indicating moisture content of hay passing past sensor 12.

According to the present improvement, the electrodes 22, 24 are attached with a baling chamber of a hay baler by the surrounding block 26 for exposing the electrodes to hay passing the baling chamber in positions extending longitudinally alongside the path of the hay. The hay moves longitudinally into the baling chamber as successive compressed charges of hay. These charges of compressed hay have an average thickness measured along their path within the baling chamber that is a function of the mechanical or hydraulic stroke of the baler and the nature of the crop being baled. To assure continuous accurate reading of moisture content across the severed ends of the crop as these compressed charges move into the baler, the length of each electrode 22, 24 should exceed the average thickness of the successive charges of hay as measured along this path. As an example, in a baler averaging 18 or 19 strokes for each forty-six inch long bale, the average thickness of the charges of hay are slightly less than three inches. Under these circumstances, it has been found that the elongated electrodes 22, 24 should be at least four inches long. Their maximum length is limited only by the unobstructed length of wall surface available along the sides of the baler, which are provided with restrictors (not shown) that prevent rearward movement of the incoming hay.

In a specific embodiment of the invention, the electrodes have been formed from stainless steel bars having a transverse cross-section one-half inch wide and approximately one-eighth inch thick. The longitudinal exposed surfaces of the electrodes are each seven inches long. They are mounted on a block 26 that is one-half inch thick and four inches wide. Block 26 is twelve inches long and protrudes longitudinally outward beyond both ends of the respective electrodes 22, 24. Electrodes 22, 24 are spaced apart in parallel side-by-side positions on block 26 by a spacing of one and one-eighth inches. The electrodes 22, 24 engage the exposed face 28 of block 26 in surface-to-surface contact, which provides structural reinforcement for the electrodes.

As can be seen in FIG. 4, the ends of each electrode 22, 24 are attached to block 26 by releasable nuts threaded about rear studs 29. Studs 29 project into recesses formed through the back of block 26, which are covered by back plate 32. Electrical connections are made by wires 19 that extend from one stud 29 on each electrode 22, 24 to the coaxial cable jack 42.

In operation, a small potential is applied across electrodes 22 and 24. When contacted by passing hay, current flows from one electrode, through the hay passing between the electrodes, and to the other electrode. The electrodes are operably connected with a resistor network. The current flow through the hay produces current through the resistive network generating a voltage representative of the moisture content of the hay. The combined thickness of block 26 and electrodes 22, 24 projects their outer exposed surfaces 25, 27 and longitudinal edge surfaces into the path of the incoming charges of hay. The compressed cut ends of the hay rub directly over electrodes 22, 24, creating a resistive shunt across them for moisture measurement purposes. This is fed to input amplifier 44, the output of which is digitized by analog to digital converter 46. the E-PROM is programmed to have the sensor sampled every two hundred (200) microseconds, store the acquired data, and then provide an arithmetic average of sixteen (16) consecutively taken samples.

The moisture/electrical resistance curve of hay is not linear. Accordingly, the processor takes incoming data and translates it into direct moisture percentage (by weight) by accessing empirical data relating to the resistance/moisture relationship of hay, which is permanently stored in memory. The direct percentage reading is then stored while fifteen (15) other readings are taken. The sixteen (16) consecutive readings are averaged and the average displayed in numeric display 18. A single cycle of obtaining and processing data for sixteen samples takes approximately two hundred milliseconds to complete. The display is updated every four seconds with a new average reading.

When baling at the rate of seven bales per minute, if each bale were forty-six inches long, the average of sixteen resistance measurements are taken over each twenty inches (approximate) along the bale as it is being formed. Accordingly, two averaged readings per bale are provided for each forty-six inch bale. As mentioned previously, further continuous averaging is assured despite variations in the size of individual incoming charges of hay because each rating is taken along more than one charge. Armed with this data, the operator can make instantaneous decisions as to the condition of the hay and as to whether or not further baling is indicated. The device is constructed to provide moisture readings from less than 10% to over 36%. Alternate programming, ranges, and processing of data could also be used without departing from the principles and scope of the invention.

Figure 6:
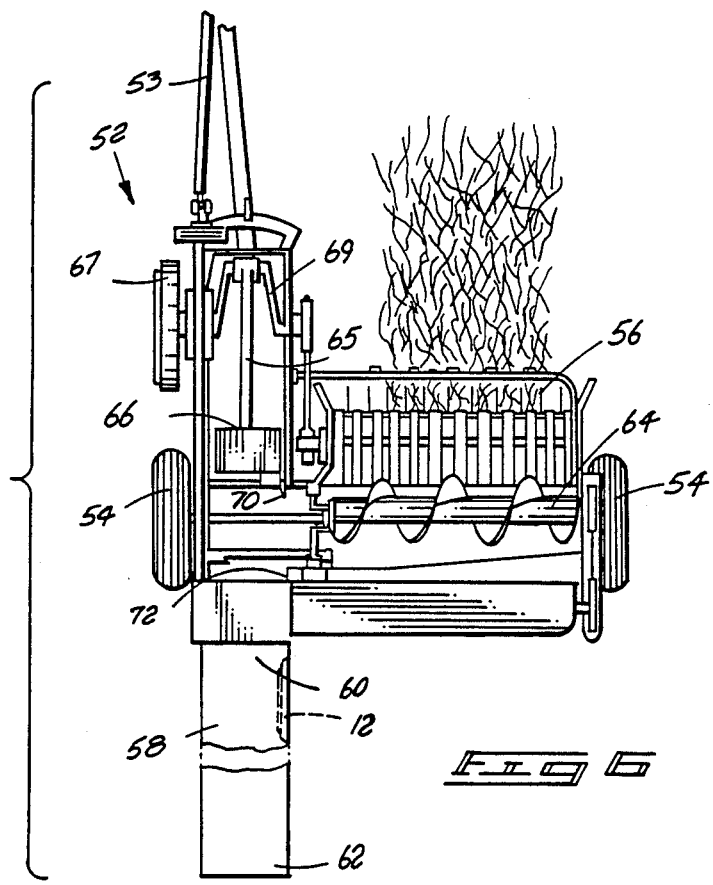
FIG. 6 is an overhead schematic view of a hay baler in accordance with the invention.

FIG. 6 illustrates a pick-up hay baler 52 and moisture sensor in accordance with the invention. The form of pick-up baler 52 as shown is just one illustrative example of a type of hay baler usable with the sensory apparatus. Any other form of a hay baler could be used such as a baler which forms round bales, without departing from the principles and scope of the invention. The components of baler 52 which tie the compressed hay into bales have been deleted for clarity. Hay baler 52 includes a framework which is supported by wheels 54. Baler 52 can be driven by an internal combustion engine mounted on the baler itself or, alternatively, it is driven by a power take-off shaft 53 from the tractor (not shown) that tows it. Removal or hay delivery means in the form of pickup prongs 56 are mounted to the framework for gathering hay from a window as hay baler 52 travels across the ground. A baling chamber or chute 58 having an entrance end 60 and an exit end 62 is mounted rearwardly and to one side of the framework. Transfer means in the form of screw auger 64 extends between pickup prongs 56 and baling chute 58 for transferring gathered hay to entrance 60 of baling chute 58.

A piston or plunger 66 is mounted to the framework for moving hay into baling chute 58. Plunger 66 is connected to a piston rod 65 and driven by means of a flywheel 67 and crankshaft 69 assembly. A plunger knife 70 is connected to the end of plunger 66 at its feed side from which auger 64 feeds hay to be subsequently forced into baling chute 58. A corresponding counter knife 72 is positioned at the same side adjacent entrance 60 of baling chute 58. As plunger 66 is forced within baling chute 60, knives 70, 72 pass very close to one another providing a scissoring-shearing action to cut protruding hay which might otherwise cause jamming.

The sensor 12 is preferably positioned within baling chute 58 as near the exit end 62 as possible on the one side adjacent which counter knife 72 is positioned. This positioning of the electrodes is preferred at the cut ends of the hay will pass past the electrodes of sensor 12 after they are cut, which will provide a reading of the moisture content of the hay. By positioning sensor 12 toward the rear of baling chute 58, one can pull the rearmost bale from the chute to expose sensor 12 for periodic visual inspection while it is in use.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

I claim:

1. A moisture sensing apparatus for monitoring the moisture content of hay by engaging the severed ends of the crop as it is being formed into a bale as successive compressed charges of hay moving longitudinally along a path within a baling chamber of a hay baler, the moisture sensing apparatus comprising:
    a pair of elongated electrodes of equal length, each electrode having longitudinal outer surfaces and edge surfaces;
    attachment means for mounting the pair of electrodes in parallel side-by-side parallel positions spaced apart from one another and adapted to extend longitudinally alongside the path of the hay within a baling chamber of a hay baler for exposing the longitudinal outer surfaces and edge surfaces of the electrodes to the severed ends of hay passing through the baling chamber;
    the attachment means comprising an elongated block of solid insulating material having an exposed planar face engaged by the elongated electrodes in surface-to-surface contact, the block of insulating material being adapted to be positioned within a baling chute with its length extending longitudinally alongside the path of the hay and with the combined thickness of the block and electrodes projecting the exposed longitudinal outer surfaces and edge surfaces of the electrodes into the path of incoming charges of hay:
    resistance monitoring means coupled to the electrodes for measuring electrical resistance in hay passing between the electrodes; and
    indication means in electrical communication with the resistance monitoring means for providing information relating to the moisture content in the hay.

2. The moisture sensing apparatus of claim 1 wherein the length of each electrode exceeds the average thickness of successive charges of hay as measured along the path.

3. A hay baler, comprising:
    a framework supported by wheels;
    hay delivery means mounted to the framework for gathering hay from a field;
    a baling chamber mounted to the framework, the baling chamber having an entrance end and an exit end;
    transfer means mounted to the framework for transferring gathered hay from the hay delivery means to the entrance of the baling chamber;
    bale forming means for compacting hay into a bale in the baling chamber as successive compressive charges of hay moving longitudinally along a path within the baling chamber; and
    moisture sensing means positioned within the baling chamber for monitoring the moisture content of the hay as it is being formed into a bale within the baling chamber, the moisture sensing means comprising:
    a pair of elongated electrodes, the electrodes being of equal length and being spaced apart in parallel side-by-side positions, each electrode having longitudinal outer surfaces and edge surfaces;
    attachment means mounting the pair of electrodes within the baling chamber in positions extending longitudinally alongside the path of the hay for exposing the longitudinal outer surfaces and edge surfaces of the electrodes to hay passing through the baling chamber;
    the attachment means comprising an elongated block of solid insulating material having an exposed planar face engaged by the elongated electrodes in surface-to-surface contact, the block of insulating material being positioned within a baling chute with its length extending longitudinally alongside the path of the hay and with the combined thickness of the block and electrodes projecting the exposed longitudinal outer surfaces and edge surfaces of the electrodes into the path of incoming charges of hay:
    resistance monitoring means coupled to the electrodes for measuring electrical resistance in hay passing between them; and
    indication means in electrical communication with the resistance monitoring means for providing information relating to the moisture content in the hay to an operator.

4. The hay baler of claim 3 wherein the length of each electrode exceeds the average thickness of successive charges of hay as measured along the path.

* * * * *